United States Patent
Buenger et al.

(10) Patent No.: US 7,048,910 B2
(45) Date of Patent: May 23, 2006

(54) USE OF ECTOINE OR ECTOINE DERIVATIVES FOR ORAL CARE

(75) Inventors: Joachim Buenger, Gross-Umstadt (DE); Hansjuergen Driller, Gross-Umstadt (DE); Olaf den Hollander, Rotterdam (NL)

(73) Assignee: Merck Patent GmbH, Darmstadt (DE)

( * ) Notice: Subject to any disclaimer, the term of this patent is extended or adjusted under 35 U.S.C. 154(b) by 70 days.

(21) Appl. No.: 10/363,789

(22) PCT Filed: Aug. 8, 2001

(86) PCT No.: PCT/EP01/09171

§ 371 (c)(1),
(2), (4) Date: Mar. 7, 2003

(87) PCT Pub. No.: WO02/19978

PCT Pub. Date: Mar. 14, 2002

(65) Prior Publication Data

US 2003/0190292 A1     Oct. 9, 2003

(30) Foreign Application Priority Data

Sep. 7, 2000     (DE) ................. 100 44 327

(51) Int. Cl.
*A61K 7/16* (2006.01)
*A61K 7/22* (2006.01)

(52) U.S. Cl. ................... 424/49; 424/54; 514/18; 514/19; 514/398; 514/399; 514/835; 514/900; 514/901; 514/902

(58) Field of Classification Search ............ 424/49–58, 424/401; 514/18, 19, 398, 399, 901
See application file for complete search history.

(56) References Cited

U.S. PATENT DOCUMENTS

| | | | |
|---|---|---|---|
| 2,649,397 A | 8/1953 | Ballard | |
| 4,346,105 A | 8/1982 | Sallmann et al. | |
| 4,529,587 A | 7/1985 | Green et al. | |
| 5,047,409 A | 9/1991 | DiSchiena et al. | |
| 5,204,099 A | 4/1993 | Barbier et al. | |
| 5,403,845 A | 4/1995 | Dunbar et al. | |
| 5,665,366 A * | 9/1997 | Rawlings et al. | 424/401 |
| 5,738,858 A | 4/1998 | Burger | |
| 5,780,042 A | 7/1998 | Gers-Barlag et al. | |
| 5,789,414 A * | 8/1998 | Lapidot et al. | 514/256 |
| 5,827,508 A | 10/1998 | Tanner et al. | |
| 5,972,718 A | 10/1999 | Moghaddam et al. | |
| 6,001,838 A * | 12/1999 | Stockhammer et al. | 514/256 |
| 6,057,282 A | 5/2000 | Desai et al. | |
| 6,060,071 A | 5/2000 | Motitschke et al. | |
| 6,153,176 A | 11/2000 | Kaleta et al. | |
| 6,267,973 B1 * | 7/2001 | Motitschke et al. | 424/401 |
| 6,403,112 B1 | 6/2002 | Motitschke et al. | |
| 6,551,917 B1 | 4/2003 | Cobbley et al. | |
| 6,602,514 B1 * | 8/2003 | Bunger et al. | 424/401 |
| 6,638,543 B1 | 10/2003 | Kang et al. | |
| 2003/0114358 A1 | 6/2003 | Galinski et al. | |
| 2003/0157040 A1 | 8/2003 | Bunger et al. | |
| 2004/0043940 A1 | 3/2004 | Bunger et al. | |

FOREIGN PATENT DOCUMENTS

| | | |
|---|---|---|
| DE | 2 132 070 | 1/1973 |
| DE | 2 154 946 | 5/1973 |
| DE | 2614723 | 4/1979 |
| DE | 2746650 | 4/1979 |
| DE | 4244580 | 7/1994 |
| DE | 43 42 560 A1 * | 6/1995 |
| DE | 4342660 | 6/1995 |
| DE | 19933460 | 1/2000 |
| DE | 19933461 | 1/2000 |
| DE | 19933463 | 1/2000 |
| DE | 19933464 | 1/2000 |
| DE | 19933466 | 1/2000 |

(Continued)

OTHER PUBLICATIONS

Chemical Abstracts 132:170870, "Cosmetic compositions containing plant extracts having moisture-retaining effects", Doi et al (Feb. 22, 2000).*

(Continued)

Primary Examiner—Frederick Krass
(74) Attorney, Agent, or Firm—Millen, White, Zelano & Branigan, P.C.

(57) ABSTRACT

The invention relates to the use of one or more compounds selected from compounds of formulae Ia and Ib, the physiologically compatible salts of compounds of formula Ia and Ib and the stereoisomer forms of compounds of formula La and Ib, wherein $R^1$, $R^2$, $R^3$, $R^4$ and n have the meaning cited in claim 1. Said compounds can be used advantageously in a preparation suitable for oral care

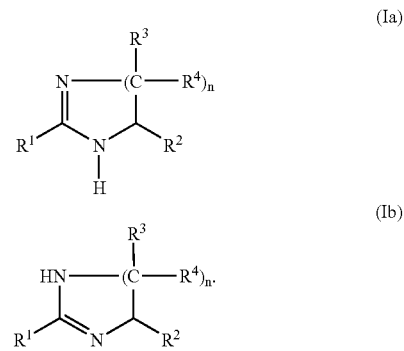

16 Claims, No Drawings

FOREIGN PATENT DOCUMENTS

| | | |
|---|---|---|
| DE | 198 34 818 | 2/2000 |
| DE | 199 11 775 | 2/2000 |
| DE | 19834818 | 2/2000 |
| DE | 10006578 | 8/2001 |
| EP | 0 888 542 | 9/1963 |
| EP | 0 275 719 | 7/1988 |
| EP | 0 553 884 | 8/1993 |
| EP | 647469 | 4/1995 |
| EP | 0 671 161 | 9/1995 |
| EP | 0915167 | 5/1999 |
| GB | 1513680 | 6/1978 |
| GB | 2114886 | 9/1983 |
| JP | 2164577 | 7/1990 |
| JP | 3086867 | 11/1991 |
| JP | 3031265 | 12/1991 |
| JP | 9143167 | 6/1997 |
| WO | WO 94 04128 | 3/1994 |
| WO | WO 94/16923 | 7/1994 |
| WO | WO 9617590 | 6/1996 |
| WO | WO 98 13020 | 4/1998 |
| WO | 0007688 | 2/2000 |
| WO | WO 0076528 | 12/2000 |
| WO | WO 0207522 | 7/2001 |
| WO | WO 0158446 | 8/2001 |
| WO | WO 0172263 | 10/2001 |
| WO | WO 0302146 | 10/2002 |

OTHER PUBLICATIONS

Chemical Abstracts 129:179959, "Betaine-containing toothpaste relieves subjective symptoms of dry mouth", Sonderling et al (1998).*
U.S. Appl. No. 08/355,275, filed Dec. 12, 1994.
U.S. Appl. No. 08/746,253, filed Nov. 7, 1996.
U.S. Appl. No. 09/834,976, filed Aprl. 16, 2001.
U.S. Appl. No. 08/953,988, filed Oct. 20, 1997.
U.S. Appl. No. 09/425,285, filed Oct. 25, 1999.
U.S. Appl. No. 09/744,766, filed Jan. 30, 2001.
U.S. Appl. No. 10/365,149, filed Jan. 31, 2003.
U.S. Appl. No. 09/744,945, filed Jan. 31, 2001.
U.S. Appl. No. 10/620,812, filed Jul. 17, 2003.
U.S. Appl. No. 09/744,767, filed Jan. 30, 2001.
U.S. Appl. No. 10/239,394, filed Sep. 23, 2002.
U.S. Appl. No. 10/239,073, filed Dec. 19, 2002.
U.S. Appl. No. 10/363,469, filed Mar. 4, 2003.
U.S. Appl. No. 10/363,789, filed Mar. 7, 2003.
Galinski et al., "1,4,5,6-Tetrahydro-2-methyl-4-pyrimidinecarboxylic Acid," *Eur. J. Biochem.* 149:136-39 (1986).
Idson, B., "Dry Skin Moisturizing and Emolliency," *Cosmetics & Toiletries* 1087:69-78 (1992).
Severin et al., "The Predominant Role of Recently Discovered Tetrahydropyrimidines For The Osmoadaptation of Halophilic Eubacteria," *Journal of General Microbiology* 138:1629-38 (1992).
STN Chemical Abstract No. 115:15263 CA of Mata "The Use of Betatine in Cosmetics and its Safety" *Frangrance, J.* 19:70-7 (1991).
DERWENT WPI week 199732 & JP 09 143167 (Jun. 3, 1997).
J. Bunger : PARfumerie und kosmetik, vol. 79, No. 11, Nov. 1998 pp. 32-35.
Sauer T. et al., "Ectoine—Biotechnische produktion und moegliche anwendungsbereiche," Git Fachzeitschrift Fuer Das Laboratorium, vol. 39, No. 10, pp. 892-896, 1995.
Buenger J., "Neue wirkstoffklasse schuetzt und pflegt die haut. ectoine stabilisieren *biopolymerstrukturen,*" *Parfumerie und Kosmetik*, vol. 79, No. 11, pp. 32-35, 1998.
DATABASE WPI, Section Ch, Week 199732, Derwent Publications Ltd,, London, (1997).
Beyer N. et al., "Ectoin—a Innovative multi-functional active substance for the cosmetic industry," SOFW Journal, vol. 128, No. 12, pp. 26, 28-29, 2000.
Krezel, I., "Antitumor activity of new derivatives of 1,3-diezaheterocycles," Pharmazie, vol. 53, No. 9, pp. 614-617, 1998.
Adams J.L. et al., "cis-4-Carboxy-6-(mercaptomethyl)-3,4,5,6-tetrahydropyrimidin-2(1H)-one, a potent inhibitor of mammalian dihydroorotase," J.Med.Chem., vol. 31, No. 7, pp. 1366-1369, 1988.

* cited by examiner

USE OF ECTOINE OR ECTOINE DERIVATIVES FOR ORAL CARE

This application is a 371 of PCT/EP01/09171, filed Aug. 8, 2001.

The invention relates to preparations for oral care.

The oral cavity of humans is colonised by a large number of commensally living bacteria, the resident microflora, which are adapted to the specific conditions in the oral chamber. The microflora of the oral cavity provides protection against colonisation by pathogenic microorganisms and is responsible for odour formation, i.e. the oral odour. The bacteria utilise the supply of nutrients in the oral cavity and on degradation of the nutrients form odorous substances, such as, for example, short-chain fatty acids. The microbial colonisation and deposition of metabolic products on the teeth favours plaque formation. The microbial degradation products of carbohydrates from food result in a reduction in the pH and support caries formation. As a consequence of acid formation by the plaque bacteria, microdecalcification of the teeth occurs. The bacteria should be protected by regular plaque removal and restriction of frequent sugar intake and/or support for recalcification by frequent fluoridation.

The object was therefore to provide preparations which are suitable for oral care.

Surprisingly, it has now been found that this object is achieved by the use of one or more compounds selected from the compounds of the formulae Ia and Ib

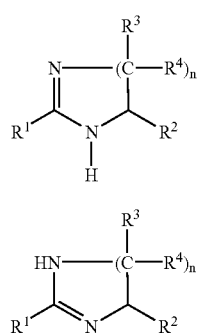

the physiologically tolerated salts of the compounds of the formulae Ia and Ib, and the stereoisomeric forms of the compounds of the formulae Ia and Ib, where $R^1$ is H or alkyl, $R^2$ is H, COOH, COO-alkyl or CO—NH—$R^5$, $R^3$ and $R^4$ are each, independently of one another, H or OH, n is 1, 2 or 3, alkyl is an alkyl radical having from 1 to 4 carbon atoms, and $R^5$ is H, alkyl, an amino acid radical, dipeptide radical or tripeptide radical, in preparations.

Ectoine protects the skin and mucous membrane microflora which are important for an intact skin barrier against stress due to drying-out, free radicals, surfactants and high ion concentration. The ectoine/hydroxyectoine does not react with the cell metabolism.

Ectoines have the property of protecting cells, proteins, enzymes, DNA and biomembranes against removal of water molecules from the hydrate shell and stabilising the spatial structure of the biopolymers.

The stabilisation of the resident oral flora by ectoine or derivatives thereof is an important prerequisite for the equilibrium of the micromedium of the oral mucous membrane and the formation of an intact oral cavity flora. Stabilisation of the resident oral flora means that transient, harmful bacteria find it more difficult to colonise.

Ectoine protects the oral mucous membrane against drying-out, surfactants and other chemicals. Colonisation of the oral mucous membrane by pathogens, such as, for example, the pus-forming organism *Staphylococcus aureus*, is hindered or prevented by stabilisation of the resident flora. The moisturiser effect additionally makes colonisation by *Staphylococcus aureus* more difficult since these bacteria bind, in particular, to collagen and fibronectin in damaged or dry skin.

The present invention relates to the use of one or more compounds selected from the compounds of the formulae Ia and Ib

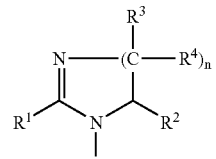

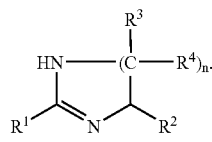

the physiologically tolerated salts of the compounds of the formulae Ia and Ib, and the stereoisomeric forms of the compounds of the formulae Ia and Ib, where $R^1$ is H or alkyl, $R^2$ is H, COOH, COO-alkyl or CO—NH—$R^5$, $R^3$ and $R^4$ are each, independently of one another, H or OH, n is 1, 2 or 3, alkyl is an alkyl radical having from 1 to 4 carbon atoms, and $R^5$ is H, alkyl, an amino acid radical, dipeptide radical or tripeptide radical, in a preparation for oral care.

For the purposes of the present invention, the preparations for oral care include compositions for oral care and for dental care.

In a preferred embodiment, the present invention relates to the use of one or more compounds selected from the above-mentioned compounds of the formulae Ia and Ib, the physiologically tolerated salts of the compounds of the formulae Ia and Ib, and the stereoisomeric forms of the compounds of the formulae Ia and Ib in preparations for the protection and care of the resident oral flora.

In a further preferred embodiment, the present invention relates to the use of one or more compounds selected from the above-mentioned compounds of the formulae Ia and Ib, the physiologically tolerated salts of the compounds of the formulae Ia and Ib, and the stereoisomeric forms of the compounds of the formulae Ia and Ib in preparations for the prophylactic protection of teeth against damage to the dental enamel.

In a further preferred embodiment, the present invention relates to the use of one or more compounds selected from the above-mentioned compounds of the formulae Ia and Ib, the physiologically tolerated salts of the compounds of the formulae Ia and Ib, and the stereoisomeric forms of the compounds of the formulae Ia and Ib in preparations for the prophylactic protection of the oral and pharyngeal mucous membrane.

The preparations comprising one or more compounds selected from the above-mentioned compounds of the formulae Ia and Ib, the physiologically tolerated salts of the compounds of the formulae Ia and Ib, and the stereoisomeric forms of the compounds of the formulae Ia and Ib are used prophylactically.

For the purposes of the present invention, all compounds above and below selected from the above-mentioned compounds of the formulae Ia and Ib, the physiologically tolerated salts of the compounds of the formulae Ia and Ib, and the stereoisomeric forms of the compounds of the formulae Ia and Ib are referred to as "ectoine or ectoine derivatives".

Ectoine and ectoine derivatives are low-molecular-weight, cyclic amino acid derivatives which can be isolated from various halophilic micro-organisms. Both ectoine and hydroxyectoine have the advantage of not reacting with the cell metabolism.

The compounds selected from the above-mentioned compounds of the formulae Ia and Ib, the physiologically tolerated salts of the compounds of the formulae Ia and Ib, and the stereoisomeric forms of the compounds of the formulae Ia and Ib can be present in the preparations in the form of optical isomers, diastereomers, racemates, zwitterions, cations or a mixture thereof. Of the compounds selected from the above-mentioned compounds of the formulae Ia and Ib, the physiologically tolerated salts of the compounds of the formulae Ia and Ib, and the stereoisomeric forms of the compounds of the formulae Ia and Ib, preference is given to those compounds in which $R^1$ is H or $CH_3$, $R^2$ is H or COOH, $R^3$ and $R^4$ are each, independently of one another, H or OH, and n is 2. Of the compounds selected from the above-mentioned compounds of the formulae Ia and Ib, the physiologically tolerated salts of the compounds of the formulae Ia and Ib, and the stereoisomeric forms of the compounds of the formulae Ia and Ib, particular preference is given to the compounds (S)-1,4,5,6-tetrahydro-2-methyl-4-pyrimidinecarboxylic acid (ectoine) and (S,S)-1,4,5,6-tetrahydro-5-hydroxy-2-methyl-4-pyrimidinecarboxylic acid (hydroxyectoine).

The term "amino acid" is taken to mean the stereoisomeric forms, for example D and L forms, of the following compounds: alanine, β-alanine, arginine, asparagine, aspartic acid, cysteine, glutamine, glutamic acid, glycine, histidine, isoleucine, leucine, lysine, methionine, phenylalanine, serine, threonine, tryptophan, tyrosine, valine, γ-aminobutyrate, Nε-acetyllysine, Nδ-acetylornithine, Nγ-acetyldiaminobutyrate and Nα-acetyldiaminobutyrate. L-amino acids are preferred.

Amino acid radicals are derived from the corresponding amino acids.

The radicals of the following amino acids are preferred: alanine, β-alanine, asparagine, aspartic acid, glutamine, glutamic acid, glycine, serine, threonine, valine, γ-aminobutyrate, Nε-acetyllysine, Nδ-acetylornithine, Nγ-acetyldiaminobutyrate and Nα-acetyldiaminobutyrate.

The di- and tripeptide radicals are acid amides from the point of view of their chemical nature and decompose on hydrolysis to give 2 or 3 amino acids. The amino acids in the di- and tripeptide radicals are bonded to one another by amide bonds. Preferred di- and tripeptide radicals are built up from the preferred amino acids.

The alkyl groups include the methyl group $CH_3$, the ethyl group $C_2H_5$, the propyl groups $CH_2CH_2CH_3$ and $CH(CH_3)_2$ and the butyl groups $CH_2CH_2CH_2CH_3$, $H_3CCHCH_2CH_3$, $CH_2CH(CH_3)_2$ and $C(CH_3)_3$. The preferred alkyl group is the methyl group.

Preferred physiologically tolerated salts of the compounds of the formulae Ia and Ib are, for example, alkali metal, alkaline earth metal or ammonium salts, such as Na, K, Mg or Ca salts, and salts derived from the organic bases triethylamine or tris(2-hydroxyethyl)amine. Further preferred physiologically tolerated salts of the compounds of the formulae Ia and Ib are formed by reaction with inorganic acids, such as hydrochloric acid, sulfuric acid and phosphoric acid, or with organic carboxylic or sulfonic acids, such as acetic acid, citric acid, benzoic acid, maleic acid, fumaric acid, tartaric acid and p-toluenesulfonic acid.

Compounds of the formulae Ia and Ib in which basic and acidic groups, such as carboxyl or amino groups, are present in the same number form internal salts.

The preparation of the compounds of the formulae Ia and Ib is described in the literature (DE 43 42 560). (S)-1,4,5,6-tetrahydro-2-methyl-4-pyrimidinecarboxylic acid and (S,S)-1,4,5,6-tetrahydro-5-hydroxy-2-methyl-4-pyrimidinecarboxylic acid can also be obtained microbiologically (Severin et al., J. Gen. Microb. 138 (1992) 1629–1638).

In a preferred embodiment, the preparation comprises one or more anti-oxidants. The preparations can comprise the antioxidants known from the specialist literature, for example flavonoids, coumaranones, amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotines (for example α-carotine, β-carotine, lycopine) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and salts thereof, diaurylthiodipropionate, distearylthiodipropionate, thiodipropionic acid and derivatives thereof (esters, ethers, peptides, lipids, nucleotides, nucleosides and salts) and sulfoximine compounds (for example buthionine sulfoximines, homocysteine sulfoximine, buthionine sulfones, penta-, hexa-, heptathionine sulfoximine), in very small tolerated doses (for example from pmol to μmol/kg), furthermore (metal) chelating agents (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives thereof (for example ascorbyl palmitate, magnesium ascorbyl phosphate, ascorbyl acetate) and coniferyl benzoate of benzoic resin, rutic acid and derivatives thereof, α-glycosylrutin, ferulic acid, furfurylideneglucitol, carnosine, butylhydroxytoluene (BHT), butylhydroxyanisole, nordohydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide).

Mixtures of antioxidants are likewise suitable for use in the preparations. Known and commercial mixtures are, for example, mixtures comprising, as active ingredients, lecithin, L-(+)-ascorbyl palmitate and citric acid (for example OXYNEX® AP), natural tocopherols, L-(+)-ascorbyl palmitate, L-(+)-ascorbic acid and citric acid (for example OXYNEX® K LIQUID), tocopherol extracts from natural sources, L-(+)-ascorbyl palmitate, L-(+)-ascorbic acid and citric acid (for example OXYNEX® L LIQUID), DL-α-tocopherol, L-(+)-ascorbyl palmitate, citric acid and lecithin (for example OXYNEX® LM) or butylhydroxytoluene (BHT), L-(+)-ascorbyl palmitate and citric acid (for example OXYNEX® 2004).

In a particularly preferred embodiment of the invention, the preparation comprises one or more compounds selected from flavonoids and/or coumaranones.

In a further particularly preferred embodiment of the invention, the preparation comprises, as antioxidant, one of the above-mentioned mixtures comprising lecithin, L-(+)-ascorbyl palmitate and citric acid (for example OXYNEX® AP), natural tocopherols, L-(+)-ascorbyl palmitate, L-(+)-ascorbic acid and citric acid (for example OXYNEX® K LIQUID), tocopherol extracts from natural sources, L-(+)-ascorbyl palmitate, L-(+)-ascorbic acid and citric acid (for example OXYNEX® L LIQUID), DL-α-tocopherol, L-(+)-ascorbyl palmitate, citric acid and lecithin (for example OXYNEX® LM) or butylhydroxytoluene (BHT), L-(+)-ascorbyl palmitate and citric acid (for example OXYNEX® 2004). Particular preference is furthermore given to embodiments comprising one of these mixtures and flavonoids.

The term flavonoids covers the glycosides of the flavanones, flavones, 3-hydroxyflavones (=flavonols), aurones, isoflavones and rotenoids [Römpp Chemie Lexikon [Römpp's Lexicon of Chemistry], Volume 9, 1993]. For the purposes of the present invention, however, it is also taken to mean the aglycones, i.e. the sugar-free constituents, and the derivatives of the flavonoids and the aglycones. For the purposes of the present invention, the term coumaranones is also taken to mean the derivatives thereof.

Preferred flavonoids are derived from flavanones, flavones, 3-hydroxyflavones, aurones and isoflavones, in particular from flavanones, flavones, 3-hydroxyflavones and aurones.

The flavanones are characterised by the following basic structure:

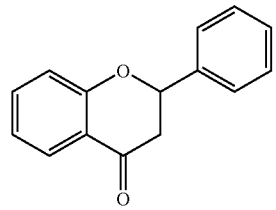

The flavones are characterised by the following basic structure:

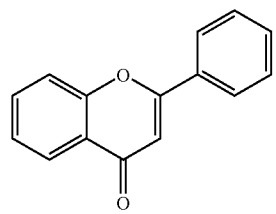

The 3-hydroxyflavones (flavonols) are characterised by the following basic structure:

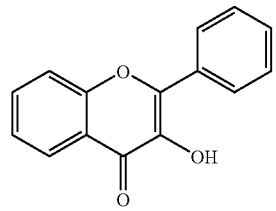

The isoflavones are characterised by the following basic structure:

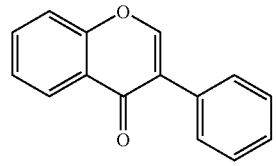

The aurones are characterised by the following basic structure:

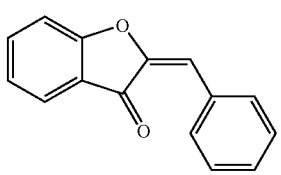

The coumaranones are characterised by the following basic structure:

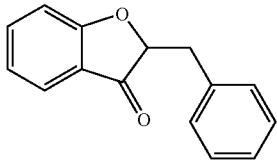

The flavonoids and coumaranones are preferably selected from the compounds of the formula (I):

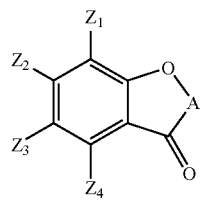

in which
- $Z_1$ to $Z_4$ are each, independently of one another, H, OH, alkoxy, hydroxyalkoxy, mono- or oligoglycoside radicals, where the alkoxy and hydroxyalkoxy groups may be branched or unbranched and can have from 1 to 18 carbon atoms, and where sulfate or phosphate may also be bonded to the hydroxy groups of the said radicals,
- A is selected from the group consisting of the subformulae (IA), (IB) and (IC)

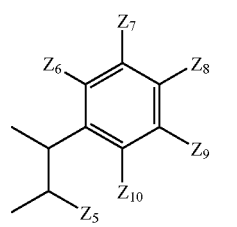

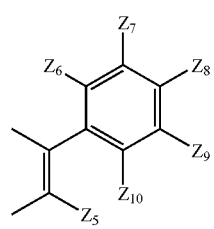

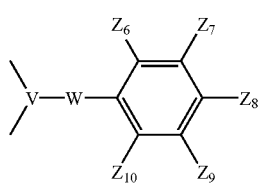

$Z_5$ is H, OH or OR,
R is a mono- or oligoglycoside radical,
$Z_6$ to $Z_{10}$ are as defined for the radicals $Z_1$ to $Z_4$, and

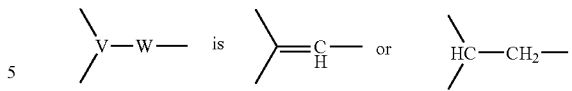

The alkoxy groups are preferably linear and have from 1 to 12 and preferably from 1 to 8 carbon atoms. These groups thus conform to the formula $—O—(CH_2)_m—H$, where m is 1, 2, 3, 4, 5, 6, 7 or 8 and in particular is from 1 to 5.

The hydroxyalkoxy groups are preferably linear and have from 2 to 12 and preferably from 2 to 8 carbon atoms. These groups thus conform to the formula $—O—(CH_2)_n—OH$, where n is 2, 3, 4, 5, 6, 7 or 8, in particular from 2 to 5 and extremely preferably 2.

The mono- and oligoglycoside radicals are preferably built up from 1 to 3 glycoside units. These units are preferably selected from the group consisting of the hexosyl radicals, in particular the rhamnosyl radicals and glucosyl radicals. However, other hexosyl radicals, for example allosyl, altrosyl, galactosyl, gulosyl, idosyl, mannosyl and talosyl, can, if desired, advantageously be used. It may also be advantageous in accordance with the invention to use pentosyl radicals.

In a preferred embodiment,
- $Z_1$ and $Z_3$ are H,
- $Z_2$ and $Z_4$ are other than H, in particular OH, methoxy, ethoxy or 2-hydroxyethoxy,
- $Z_5$ is H, OH or OR, where R is a glycoside radical which is built up from 1 to 3, preferably 1 or 2, glycoside units,
- $Z_6$, $Z_9$ and $Z_{10}$ are H, and
- $Z_7$ and $Z_8$ are other than H, in particular OH, methoxy, ethoxy or 2-hydroxyethoxy.

In a further particularly preferred embodiment of the invention, in particular if the water solubility of the flavonoids and coumaranones is to be increased, a sulfate or phosphate group is bonded to the hydroxyl groups. Suitable counterions are, for example, the ions of the alkali or alkaline earth metals, these being selected, for example, from sodium and potassium.

The flavonoids are preferably selected from the following compounds: 4,6,3',4'-tetrahydroxyaurone, quercetin, rutin, isoquercetin, eriodictyol, taxifolin, luteolin, trishydroxyethylquercetin (troxequercetin), trishydroxyethylrutin (troxerutin), trishydroxyethylisoquercetin (troxeisoquercetin), trishydroxyethylluteolin (troxeluteolin) and sulfates and phosphates thereof.

Of the flavonoids, particular preference is given to rutin and troxerutin. Very particular preference is given to troxerutin.

Of the coumaranones, preference is given to 4,6,3',4'-tetrahydroxybenzyl-3-coumaranone.

The proportion of the one or more antioxidants in the preparation is preferably from 0.001 to 5% by weight, particularly preferably from 0.01 to 2% by weight, based on the preparation as a whole.

Furthermore, the preparations may also comprise, for example, anthocyanidine (cyanidine).

The preparations are prepared by converting one or more compounds selected from the above-mentioned compounds of the formulae Ia and Ib, the physiologically tolerated salts of the compounds of the formulae Ia and Ib, and the stereoisomeric forms of the compounds of the formulae Ia and Ib into a suitable preparation form, if desired with adjuvants and/or excipients. The adjuvants and excipients originate from the group consisting of the vehicles, preservatives and other conventional assistants.

The preparations based on one or more compounds selected from the above-mentioned compounds of the formulae Ia and Ib, the physiologically tolerated salts of the compounds of the formulae Ia and Ib, and the stereoisomeric forms of the compounds of the formulae Ia and Ib are used in the adminstration forms which are conventional in oral and pharyngeal hygiene.

Suitable use forms are all administration forms used for oral hygiene, for example solutions, emulsions, suspensions, such as, for example, pastes, gels, surfactant-containing cleaning preparations and sprays, such as, for example, aerosol sprays and pump sprays. In addition to the one or more compounds selected from the above-mentioned compounds of the formulae Ia and Ib, the physiologically tolerated salts of the compounds of the formulae Ia and Ib, and the stereoisomeric forms of the compounds of the formulae Ia and Ib, any desired conventional excipients, adjuvants and, if desired, further active ingredients can be added to the preparation.

Preferred adjuvants originate from the group consisting of the preservatives, antioxidants, stabilisers, solubilisers, vitamins, colorants, odour improvers, thickening agents, humectants, abrasives and scouring media, foaming agents, thickeners, binders and flavours.

Besides one or more compounds selected from the above-mentioned compounds of the formulae Ia and Ib, the physiologically tolerated salts of the compounds of the formulae Ia and Ib, and the stereoisomeric forms of the compounds of the formulae Ia and Ib, solutions and emulsions can comprise the conventional excipients, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular essential oils, such as peppermint oil, clove oil, aniseed oil, fennel oil, sage oil, glycerol fatty acid esters, hydrogenated castor oils, polyethylene glycols and fatty acid esters of sorbitan, polysorbates or mixtures of these substances.

The emulsions can exist in various forms. For example, they can be, for example, an emulsion or microemulsion of the water-in-oil (W/O) type or of the oil-in-water (O/W) type, or a multiple emulsion, for example of the water-in-oil-in-water (W/O/W) type.

The preparations may also be in the form of emulsifier-free, disperse preparations. They can be, for example, hydrodispersions or Pickering emulsions.

Besides one or more compounds selected from the above-mentioned compounds of the formulae Ia and Ib, the physiologically tolerated salts of the compounds of the formulae Ia and Ib, and the stereoisomeric forms of the compounds of the formulae Ia and Ib, suspensions can comprise the conventional excipients, such as liquid diluents and humectants, for example water, ethanol or propylene glycol, sorbitol, glycerol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Besides one or more compounds selected from the above-mentioned compounds of the formulae Ia and Ib, the physiologically tolerated salts of the compounds of the formulae Ia and Ib, and the stereoisomeric forms of the compounds of the formulae Ia and Ib, gels can comprise the conventional excipients, for example animal and vegetable fats, waxes, paraffins, starch, tragacanth, cellulose derivatives, polyethylene glycols, silicones, bentonites, silica, talc and zinc oxide, or mixtures of these substances.

Besides one or more compounds selected from the above-mentioned compounds of the formulae Ia and Ib, the physiologically tolerated salts of the compounds of the formulae Ia and Ib, and the stereoisomeric forms of the compounds of the formulae Ia and Ib, surfactant-containing cleaning products can comprise the conventional excipients, such as salts of fatty alcohol sulfates, fatty alcohol ether sulfates, sulfosuccinic acid monoesters, fatty acid albumen hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Besides one or more compounds selected from the above-mentioned compounds of the formulae Ia and Ib, the physiologically tolerated salts of the compounds of the formulae Ia and Ib, and the stereoisomeric forms of the compounds of the formulae Ia and Ib, sprays can comprise the conventional excipients, for example lactose, talc, silica, aluminium hydroxide, calcium silicate and polyamide powders, or mixtures of these substances. They may additionally comprise the conventional propellants, for example chlorofluorocarbons, propane/butane or dimethyl ether.

The oral and dental care compositions can be, for example, in the form of toothpastes, liquid tooth creams, tooth powders, mouthwashes or, if desired, also in the form of a chewing composition, for example in the form of chewing gum. However, they are preferably in the form of more or less flowable or plastic toothpastes, as are used for cleaning teeth using a toothbrush.

The toothpastes or liquid tooth creams comprise a polishing agent, usually in an amount of from 5 to 50% by weight, and a humectant, usually in an amount of 10–60% by weight.

Suitable polishing agents are all abrasive media which are known for toothpastes, such as, for example, silicas, aluminium hydroxide, aluminium oxide, calcium pyrophosphate, chalk, dicalcium phosphate dihydrate ($CaHPO_4 \cdot 2H_2O$), sodium aluminium silicates, such as, for example, zeolite A, organic polymers, such as, for example, polymethacrylate, or mixtures of these abrasive media.

Suitable vehicles for the toothpastes, which enable a suitable consistency to be established for dispensing from tubes, dispensing containers or flexible bottles, are, for example, a combination of humectants, binders and water.

Humectants which can be employed are, for example, glycerol, sorbitol, xylitol, propylene glycols, polyethylene glycols, in particular those having mean molecular weights of 200–800. The consistency regulators (or binders) used are, for example, natural and/or synthetic water-soluble polymers, such as alginates, carragheenates, tragacanth, starch and starch ethers, cellulose ethers, such as, for example, carboxymethylcellulose (Na salt), hydroxyethylcellulose, methylhydroxypropylcellulose, guar, acacia gum, agar-agar, xanthan gum, succinoglycan gum, carob-seed flour, pectins, water-soluble carboxyvinyl polymers (for example CARBOPOL® grades), polyvinyl alcohol, polyvinylpyrrolidone, polyethylene glycols, in particular those having molecular weights of 1500–1,000,000.

Further substances which are suitable for viscosity control are, for example, phyllosilicates, such as, for example, montmorillonite clays, colloidal thickening silicas, such as, for example, aerogel silicas, pyrogenic silicas or microground precipitation silicas. It is also possible to use viscosity-stabilising additives from the group consisting of cationic, zwitterionic or ampholytic nitrogen-containing surfactants, hydroxypropyl-substituted hydrocolloids or polyethylene glycol-polypropylene glycol copolymers having a mean molecular weight of from 1000 to 5000, or a combination of the said compounds, in the toothpastes.

In order to support the cleaning action and if desired also for the development of foam during tooth brushing and for stabilisation of the polishing media dispersion in the vehicle, the toothpastes also comprise surface-active substances in an amount of 0.1–5% by weight.

Suitable surfactants are, for example, linear sodium alkylsulfates having 12–18 carbon atoms in the alkyl group. These substances additionally have an enzyme-inhibiting action on the bacterial metabolism of plaque. Further suitable surfactants are alkali metal salts, preferably sodium salts, of alkylpolyglycol ether sulfate having 12–16 carbon atoms in the linear alkyl group and 2–6 glycol ether groups in the molecule, of linear alkane($C_{12}$–$C_{18}$)sulfonate, of sulfosuccinic acid monoalkyl($C_{12}$–$C_{18}$)esters, of sulfated fatty acid monoglycerides, sulfated fatty acid alkanolamides, sulfoacetic acid alkyl($C_{12}$–$C_{16}$)esters, alkylsarcosines, acyltaurides and acylisothionates, each having 8–18 carbon atoms in the acyl group. Also suitable are zwitterionic, ampholytic and nonionic surfactants, for example oxyethylates of fatty acid mono- and diglycerides, of fatty acid sorbitan esters and alkyl(oligo)glucosides.

Further conventional additives to the oral and dental care compositions, in particular to toothpastes, are
- sweeteners, such as, for example, saccharin-sodium, sodium cyclamate, sucrose, lactose, maltose and fructose,
- flavours, such as, for example, peppermint oil, spearmint oil, eucalyptus oil, aniseed oil, fennel oil, caraway seed oil, menthyl acetate, cinnamaldehyde, anethole, vanillin, thymol, and mixtures of these and other natural and synthetic flavours,
- pigments, such as, for example, titanium dioxide,
- dyes,
- buffer substances, such as, for example, primary, secondary or tertiary alkali metal phosphates or citric acid/sodium citrate.

The oral and dental care compositions, in particular the toothpastes, may comprise other active ingredients in addition to ectoine.

The oral and dental care compositions, in particular the toothpastes, may comprise, for example, anticaries active ingredients. These can be selected, for example, from organic and inorganic fluorides, for example from sodium fluoride, potassium fluoride, sodium monofluorophosphate, tin fluoride and sodium fluorosilicate.

The oral and dental care compositions, in particular the toothpastes, may also comprise, for example, substances which are effective against tartar. Substances of this type can be, for example, chelating agents, such as, for example, ethylenediaminetetraacetic acid and sodium salts thereof, pyrophosphate salts, such as the water-soluble dialkali metal or tetraalkali metal pyrophosphate salts, for example $Na_4P_2O_7$, $K_4P_2O_7$, $Na_2K_2P_2O_7$, $Na_2H_2P_2O_7$ and $K_2H_2P_2O_7$, or polyphosphate salts, which can be selected, for example, from water-soluble alkali metal tripolyphosphates, such as sodium tripolyphosphate and potassium tripolyphosphate.

The oral and dental care compositions, in particular the toothpastes, may also comprise, for example, antimicrobial substances as preservatives or as antiplaque active ingredients. Substances of this type can be selected, for example, from methyl, ethyl or propyl p-hydroxybenzoate, sodium sorbate, sodium benzoate, bromochlorophen, triclosane, phenylsalicylic acid esters, biguanides, for example chlorhexidine, thymol, etc.

The oral and dental care compositions, in particular the toothpastes, may also comprise, for example, wound-healing and inflammation-inhibiting substances, for example active ingredients against gum inflammation. Substances of this type may be selected, for example, from allantoin, azulene, camomile extracts, tocopherol, panthenol, bisabolol and sage extracts.

The oral and dental care compositions, in particular the toothpastes, may also comprise substances for increasing the mineralisation potential, for example calcium-containing substances, such as, for example, calcium chloride, calcium acetate and dicalcium phosphate dihydrate. The concentration of the calcium-containing substance depends on the solubility of the substance and on the interaction with other substances present in the oral and dental care composition.

The oral and dental care compositions, in particular the toothpastes, may also comprise substances which increase the insensitivity of the teeth, for example potassium salts, such as, for example, potassium nitrate, potassium citrate, potassium chloride, potassium bicarbonate and potassium oxalate.

In mouthwashes, the vehicle essentially consists of water, ethanol, essential oils, emulsifiers and solubilisers for the ectoine and the flavour components, flavour correctants (for example sweeteners) and, if desired, astringent or invigorating drug extracts and, if desired, dyes. Further active ingredients which may be present are, for example, antimicrobial substances, such as chlorhexidine or triclosane.

In a further preferred embodiment, the preparation comprises one or more enzymes. The enzyme(s) is (are) preferably selected from the group consisting of glucose oxidase, amyloglucosidase and lactoperoxidase. The enzymes may have, for example, an antiplaque activity. For example, the addition of the enzyme glucose oxidase during oxidative glucose degradation may result in the liberation of hydrogen peroxide, thus combating plaque.

However, enzymes frequently have low stability and are exposed in vitro to a number of destabilising conditions. For example, substances of this type are sensitive to changes in the medium surrounding them and to temperature variations. The storage of enzymes over an extended period therefore results in a decrease in activity. The use of enzymes in preparations for oral care is particularly difficult since these products are subjected to large temperature and humidity variations. Destabilisation of the enzymes can thus occur before they reach the site of action from the preparation.

The problem of the decrease in the activity of enzymes also arises, in particular, in preparations in which they have to have the highest possible activity over an extended period. This is the case, for example, in preparations with uniform liberation of the enzymes over an extended period, which is also known as the "depot effect".

For the above-mentioned reasons, it is necessary to stabilise enzymes in preparations. It has been found that the stabilisation of enzymes present in preparations for oral care is achieved by the compounds selected from the above-mentioned compounds of the formulae Ia and Ib, the physiologically tolerated salts of the compounds of the formulae Ia and Ib, and the stereoisomeric forms of the compounds of the formulae Ia and Ib which are like-wise present in the preparation.

The proportion of the compounds selected from the above-mentioned compounds of the formulae Ia and Ib, the physiologically tolerated salts of the compounds of the formulae Ia and Ib, and the stereoisomeric forms of the compounds of the formulae Ia and Ib in the preparation is preferably from 0.001 to 50% by weight, particularly preferably from 0.01 to 10% by weight and especially preferably from 0.1 to 10% by weight, based on the preparation as a whole.

All compounds or components which can be used in the preparations are either known and commercially available or can be synthesised by known methods.

The following examples serve to illustrate the invention and are in no way to be regarded as a limitation. All % data are per cent by weight.

The INCI names of raw materials used are as follows:

| Raw material | INCI name |
| --- | --- |
| Karion F liquid | Sorbitol, Aqua |
| Peppermint aroma | Aroma |
| Phoskadent NA 211 | Sodium Monofluorophosphate |
| Polyethylene glycol 400 DAB | PEG-8 |
| RonaCare ™ CPC | N-Cetylpyridinium Chloride Monohydrate |
| RonaCare Ectoine | Ectoine |
| RonaCare NaF | Sodium Fluoride |
| RonaCare ™ Olaflur | Bis(hydroxyethyl)aminopropyl-N-hydroxy-ethyl-octadecylamine dihydrofluoride, 33% in 1,2-propanediol |
| Sident 12 | Silica |
| Sipernat 22 S | Hydrated Silica |
| Tego Betaine BL 215 | Cocamidopropyl Betaine |
| Tego Betaine F 50 | Cocamidopropyl Betaine |
| Tego Betaine ZF | Cocamidopropyl Betaine |
| Trihydroxyethylrutin | Troxerutin |

EXAMPLE 1

A mouthwash concentrate comprising ectoine is prepared from the following components:

| | | | % by wt. |
| --- | --- | --- | --- |
| RonaCare ™ CPC | (Art. No. 102340) | (1) | 0.2 |
| RonaCare ™ Olaflur | (Art. No. 11680) | (1) | 0.5 |
| RonaCare ™ Ectoine | (Art. No. 130200) | (1) | 1.0 |
| Ethanol (96%) | (Art. No. 100971) | (1) | 20.0 |
| Menthol | (Art. No. 105995) | (1) | 0.2 |
| Tego-Betaine BL 215 | | (2) | 5.0 |
| Glycerol (87%) | (Art. No. 104091) | (1) | 12.0 |
| Water, demineralised | | | to 100 |

Preparation:

Phase A is stirred until a clear solution is formed.

Sources of Supply:
(1) Merck KGaA
(2) Goldschmidt AG

EXAMPLE 2

A tooth gel comprising ectoine is prepared from the following components:

| | | | | | % by wt. |
| --- | --- | --- | --- | --- | --- |
| A | RonaCare NaF | (Art. No. 106441) | (1) | 0.1 |
| | RonaCare Ectoine | (Art. No. 130200) | (1) | 1.0 |
| | Sodium benzoate | (Art. No. 106290) | (1) | 0.2 |
| | Sodium saccharin | (Art. No. 817042) | (1) | 0.2 |
| | Phoskadent | | (2) | 0.75 |
| | Karion F liquid | (Art. No. 102993) | (1) | 65.0 |
| | Water, demineralised | | | to 100 |
| B | Bromochlorophene | (Art. No. 103281) | (1) | 0.1 |
| | Peppermint aroma 77526-34 | | (3) | 1.0 |
| | Polyethylene glycol 400 DAB | | (3) | 3.0 |
| C | Sident 12 | | (4) | 8.5 |
| | Sipernat 22 S | | (4) | 7.5 |
| D | Pearlescent pigments | | (1) | 0.05 |
| | Tego-Betaine F 50 | | (5) | 5.0 |

Preparation:

Phases A and B are pre-mixed separately from one another and combined. Phase C is then slowly added with stirring, and the mixture is subsequently warmed to 50° C. under reduced pressure. Phase D is added to the clear gel, the mixture is stirred slowly under reduced pressure until free from air, and then allowed to cool to room temperature.

Sources of Supply:
(1) Merck KGaA
(2) Benckiser-Knapsack GmbH
(3) Givaudan-Roure GmbH
(4) Degussa AG
(5) Th. Goldschmidt AG

EXAMPLE 3

A tooth gel comprising ectoine is prepared from the following components:

| | | | % by wt. |
| --- | --- | --- | --- |
| A | RonaCare ™ NaF | (1) | 0.08 |
| | RonaCare ™ Ectoine | (1) | 1.00 |
| | Trihydroxyethylrutin | (1) | 0.50 |
| | Karion F liquid | (1) | 62.13 |
| | Sodium benzoate | (1) | 0.20 |
| | Sodium saccharinate | | 0.20 |
| | Water, demineralised | | 9.00 |
| B | RonaCare ™ Olaflur | (1) | 1.50 |
| | Bromochlorophene | (1) | 0.10 |
| | Aroma 35049 | (2) | 1.00 |
| C | Polyethylene glycol 400 | (1) | 3.00 |
| | Tego Betaine ZF | (3) | 5.00 |
| | Sicomet Patent Blue (E131), 0.1% in Water | (4) | 0.80 |
| | | | to 100 |
| D | Sident 12 | (5) | 9.50 |
| | Sipernat 22 S | (5) | 7.50 |

Preparation:

Phases A and B are pre-mixed separately from one another. Phase C is heated to 50° C., phases A and B are stirred into phase C, and the phases are subsequently mixed under reduced pressure. After slow addition of phase D, the mixture is homogenised under reduced pressure. Stirring is continued under reduced pressure until the gel is clear.

Sources of Supply:
(1) Merck KGaA
(2) Orissa Drebing GmbH
(3) Th. Goldschmidt AG (4) BASF AG (5) Degussa AG.

The invention claimed is:

1. A method for the protection and care of resident oral flora comprising administering an oral care composition to the oral cavity of a subject in need thereof, said composition comprising a compound of formula Ia or Ib, or a physiologically acceptable salt thereof,

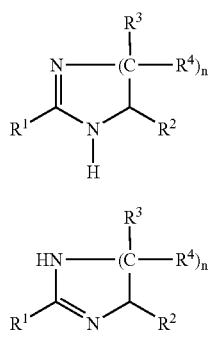

wherein, $R^1$ is H or alkyl, $R^2$ is H, COOH, COO-alkyl or CO—NH—$R^5$, $R^3$ and $R^4$ are each, independently of one another, H or OH, n is 1, 2 or 3, alkyl is an alkyl radical having from 1 to 4 carbon atoms, and $R^5$ is H, alkyl, an amino acid radical, dipeptide radical or tripeptide radical.

2. A method for the protection of teeth against damage to the dental enamel comprising administering an oral care composition to the oral cavity of a subject in need thereof, said composition comprising a compound of formula Ia or Ib, or a physiologically acceptable salt thereof,

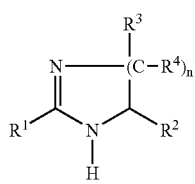

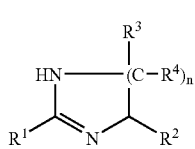

wherein, $R^1$ is H or alkyl, $R^2$ is H, COOH, COO-alkyl or CO—NH—$R^5$, $R^3$ and $R^4$ are each, independently of one another, H or OH, n is 1, 2 or 3, alkyl is an alkyl radical having from 1 to 4 carbon atoms, and $R^5$ is H, alkyl, an amino acid radical, dipeptide radical or tripeptide radical.

3. A method according to claim 1, wherein the oral care composition is in the form of a solution, an emulsion, a suspension, a paste, a gel, a surfactant-containing cleaning preparation, a spray, a cream, a powder, a mouthwash or a chewing composition.

4. A method according to claim 1, wherein the oral care composition comprises 0.001 to 50% by weight, a compound of formula Ia or Ib, or a physiologically acceptable salt thereof, based on the composition as a whole.

5. A method according to claim 1, wherein the compound of formula Ia or Ib is (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid.

6. A method according to claim 1, wherein the oral care composition further comprises one or more antioxidants.

7. A method according to claim 1, wherein the oral care composition further comprises one or more enzymes.

8. A method according to claim 2, wherein the oral care composition is in the form of a solution, an emulsion, a suspension, a paste, a gel, a surfactant-containing cleaning preparation, a spray, a cream, a powder, a mouthwash or a chewing composition.

9. A method according to claim 2, wherein the oral care composition comprises 0.001 to 50% by weight, a compound of formula Ia or Ib, or a physiologically acceptable salt thereof, based on the composition as a whole.

10. A method according to claim 2, wherein the compound of formula Ia or Ib is (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid.

11. A method according to claim 2, wherein the oral care composition further comprises one or more antioxidants.

12. A method according to claim 2, wherein the oral care composition further comprises one or more enzymes.

13. A method according to claim 1, wherein the oral care composition further comprises glucose oxidase, amyloglucosidase or lactoperoxidase.

14. A method according to claim 2, wherein the oral care composition further comprises glucose oxidase, amyloglucosidase or lactoperoxidase.

15. A method according to claim 7, wherein the enzyme has antiplaque activity, and optionally liberates hydrogen peroxide.

16. A method according to claim 12, wherein the enzyme has antiplaque activity, and optionally liberates hydrogen peroxide.

* * * * *